US006946585B2

(12) United States Patent
London Brown

(10) Patent No.: US 6,946,585 B2
(45) Date of Patent: Sep. 20, 2005

(54) ABSORBENT ARTICLE

(75) Inventor: Allison London Brown, New Hope, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 60 days.

(21) Appl. No.: 09/880,175

(22) Filed: Jun. 13, 2001

(65) Prior Publication Data

US 2002/0049418 A1 Apr. 25, 2002

Related U.S. Application Data

(60) Provisional application No. 60/242,553, filed on Oct. 23, 2000.

(51) Int. Cl.⁷ ................................................ A61F 13/15
(52) U.S. Cl. ..................................................... 604/378
(58) Field of Search ......................................... 604/378

(56) References Cited

U.S. PATENT DOCUMENTS

| | | | |
|---|---|---|---|
| 3,554,195 A | * 1/1971 | Murdoch ..................... 604/365 |
| 4,777,073 A | 10/1988 | Sheth | |
| 5,236,963 A | 8/1993 | Jacoby et al. | |
| 5,462,538 A | 10/1995 | Korpman | |
| 5,594,070 A | 1/1997 | Jacoby et al. | |
| 5,681,305 A | 10/1997 | Korpman | |
| 5,865,823 A | * 2/1999 | Curro ......................... 604/367 |
| 5,885,681 A | 3/1999 | Korpman | |
| 6,087,551 A | 7/2000 | Pereira | |
| 6,101,776 A | * 8/2000 | Conley ........................ 52/379 |
| 6,198,018 B1 | * 3/2001 | Curro ......................... 604/367 |
| 6,286,145 B1 | * 9/2001 | Welchel et al. .................. 2/69 |
| 6,446,495 B1 | * 9/2002 | Herrlein et al. ................. 73/73 |
| 6,534,083 B2 | * 3/2003 | Gilding et al. .............. 424/443 |

FOREIGN PATENT DOCUMENTS

| | | |
|---|---|---|
| EP | 0 283 200 A2 | 9/1988 |
| EP | 0 887 058 A1 | 12/1998 |
| WO | WO 99/18903 A1 | 4/1999 |

OTHER PUBLICATIONS

EPO Search Report dated Jan. 14, 2004, for corresponding EP 01308963.6.

* cited by examiner

*Primary Examiner*—Larry I. Schwartz
*Assistant Examiner*—C. Lynne Anderson

(57) ABSTRACT

An absorbent article having an absorbent core and a backsheet, wherein the backsheet has a MVTR of from about 5800 to about 10000 g/m²/24 hrs. and a basis weight of less than about 32 g/m².

16 Claims, No Drawings

ABSORBENT ARTICLE

This application claims the benefit of Provisional Application No. 60/242,553, filed Oct. 23, 2000.

This invention relates to an absorbent article, such as pantiliner, sanitary napkin, incontinence pad and wound care article, including surgical dressing and adhesive bandage. More particularly, the present invention relates to a pantiliner that is vapor permeable and liquid impermeable.

BACKGROUND OF THE INVENTION

Absorbent articles receive body exudates, including fluids and solids. Absorbent articles function both to contain the discharged materials and to isolate these materials from the body of the wearer and from the wearer's garments and the environment. Absorbent articles having many different basic designs are known and include diapers, sanitary napkins, pantiliners, and wound care articles, including surgical dressings and adhesive bandages.

Typically, an absorbent article has three major components: a top sheet, an outer backsheet and an absorbent core therebeteween. In normal use, the top sheet contacts the wearer's skin and provides channels to transport body fluids to the absorbent core. The absorbent core functions to retain the body exudates. The backsheet contacts the wearers' clothing or garment and is typically a flexible, fluid and vapor impervious sheet that prevents absorbed fluid from soiling the wearer's clothing, bedding and the like.

Specifically, the backsheet is often constructed from fluid impervious films, such as those made from polyolefins, e.g., polyethylene and polypropylene. Although such backsheets do prevent fluid from passing through the absorbent article, they also can make the wearer of the absorbent article uncomfortable due to their impermeability to air and/or moisture vapor. Surprisingly, it has been found that a microporous film having a low basis weight and high MVTR values can be used in a variety of absorbent articles to increase the wearer's comfort and promote skin and body wellness.

SUMMARY OF THE INVENTION

An absorbent article having an absorbent core and a backsheet, wherein the backsheet has a MVTR of from about 5800 to about 10000 $g/m^2/24$ hrs. and a basis weight of less than about 32 $g/m^2$. are described herein.

DETAILED DESCRIPTION OF THE INVENTION

The absorbent articles of this invention, include, but are not limited to disposable diapers, sanitary napkins, tampons, s, wound care articles, including surgical dressing and adhesive bandages and the like.

As used herein, terms such as "less than," "or less," "greater than," "or greater," and the like are intended to include disclosure of all numbers not expressly recited. For example, a recitation of "100 or less" is intended to include an express disclosure of, for example, 24, 33, 45.01, 67.499922, 1, 0.002352, 99.9999999, 100, and the like.

As is well known to those skilled in the art, absorbent articles that are worn externally generally have a layered construction with a body-facing surface that is oriented to face the wearer during use and a garment-facing surface oriented in the opposite direction from the body-facing surface. Typically such articles have a liquid pervious cover on the body-facing surface of the article, an absorbent core and a backsheet on the garment-facing surface of the article. The absorbent core is interposed between the cover and the backsheet. The cover and the backsheet encase all components of the article. The cover and the backsheet are joined or sealed to each other along their peripheral edge using methods described below. Additional components that also extend to the peripheral edge of the article can be also joined or sealed to the peripheral edge of the cover and/or backsheet. These peripheral joinders do not replace the adhesive attachments within the article.

In accordance with an embodiment of the present invention, there is provided a novel absorbent article, having a body-facing fluid permeable cover sheet, a fluid impermeable backsheet, which in the case of sanitary products face the users garment when in use, and an absorbent core between the cover sheet and the backsheet.

The liquid permeable cover of the absorbent article may be formed from any fluid pervious material that is comfortable against the skin and permits fluid to penetrate to the absorbent core. The cover should retain little or no fluid in its structure in order to provide a relatively dry surface next to the skin. The cover may be a fibrous fabric made of fibers, including bicomponent fibers, or filaments of polymers, such as polyethylene, polypropylene, polyester, or cellulose. Alternatively, the cover may be formed from an apertured film, plastic nets, webs and the like. Any of these materials may be used.

In an embodiment, the cover is a non-woven fabric formed from an interconnected network thermoplastic polymer fibers, at least a portion of the non-woven fabric having a three-dimensional thickness profile having a plurality of raised regions, semi-raised regions, and compressed regions. The raised regions having a lower fiber density relative to the semi-raised regions and the semi-raised regions having a lower fiber density relative to the compressed regions. See, for example, U.S. Pat. No. 6,087,551, which is incorporated herein by reference in its entirety.

The absorbent core can be a fluffy batt cut from a relatively loose web of non-woven fibers having a relatively high absorptive capacity. The absorbent core usually has a rectangular configuration, and may optionally have inwardly curved side edges, such as an hourglass shape. The absorbent core is usually smaller than the backing sheet and the cover. The absorbent core may also be a fibrous batt having an integral densified layer. In such a case, the absorbent core is positioned on the backing sheet of the absorbent article so that the densified layer adjoins the backing sheet. The densified layer has relatively higher wettability and liquid retentivity than the rest of the aforesaid batt and usually is formed by slightly moistening one surface of the batt and thereafter compressing the moistened surface.

The absorbent core may contain any material that absorbs bodily secretions including, but not limited to pulp, polymeric fibers and filaments, spagnum moss, natural fibers, superabsorbent polymers (including fibers, particulate material and foams), absorbent foams, and other such absorbent materials. The absorbent core is cellulosic fibers and superabsorbent polymer particles. The absorbent core may also include additional materials such as odor control material, wetness indicator material, materials for administering or delivering medicaments, such as encapsulated medicaments, and materials for maintaining skin moisture, such as encapsulated moisturizers.

The cover and backsheet are usually substantially coextensive and are joined together about the periphery of the absorbent article. Additionally, the absorbent core may be anchored to the cover, backsheet or other components of the absorbent article. Methods for attaching the components together are included in the discussion of adhesives.

The backsheet may be of any flexible material that prevents the transfer of fluid through it, but does not necessarily prevent the passages of gases. Backsheets that are pervious to vapor are known as breathable backsheets. In general, these backsheets are intended to allow the passage of vapor through them while retarding, at least to a degree, the passage of fluid. Porous film technology provides materials that can be used to form sheets that allow vapor transmission, but are relatively impervious to liquids. Commonly used materials are polyethylene or polypropylene films. Other materials that may be used as impermeable barriers may be chosen from films of polyesters, polyamides, polyethylene vinyl acetate, polyvinyl chloride, and polyvinylidene chloride. Co-extruded and laminated combinations of the foregoing, wherein such combinations are permitted by the chemical and physical properties of the film, may be used. Fluid impermeable nonreticulated foams and repellent treated papers may also be used. Films that are fluid barriers, but permit gases to transpire, i.e., "breathable films," may also be used. These include in particular, porous or microporous films, as previously described. The gasses most commonly used to demonstrate a film's breathability are water vapor, sometimes referred to as moisture vapor, and oxygen.

The moisture vapor transmission rate test ("MVTR") measures the mass or volume of gas transported across the cross section of the film in a given unit of time at a defined set of environmental conditions. While the mechanism of gas transfer often differs from film to film, it is the total amount of gas that passes through the film that makes films breathable.

When in close proximity to the skin, high MVTR films allow the body to cool itself naturally, e.g., excess moisture to evaporate. When a high MVTR film also provides a barrier to liquid transfer and/or microbial transfer, there are a variety of applications, most of which are in direct or indirect contact with skin, that can take advantage of this unique combination of properties.

A suitable backsheet material can be a microporous sheet made from polyolefin or blends thereof. In an embodiment, the backsheet is a microporous sheet made from a blend of a linear low-density polyethylene, a low density polyethylene and a calcium carbonate filler. Additionally, other components, such as antioxidants and pigments, may be added to the blend.

In particular, microporous films have been made by incorporating filler particles into a polymer and stretching the resulting material to form a film having voids induced by the filler particles. Incorporating filler particles into a polymer introduces a range of variables for consideration. Such variables include the type of filler, the amount of filler, the filler particle size and size distribution, surface-modifications of the filler particles, the mode or method of stretching the film, and the like. Each of these variables can affect the morphology and properties of the resulting film.

In process of making the film, the components are blended, extruded and embossed. The resultant film can then be stretched and heat-cured. Such methods are known, see for example, U.S. Pat. No. 4,777,073, which is incorporated herein by reference in its entirety. A film made according to the above methodology, as used in the present invention, is a single layer film having a low basis weight, a high breathability and is heat sealable.

In particular, the breathable film used in the present invention has a basis weight of about 32 $g/m^2$ or less, about 30 $g/m^2$ or less, or about 28–30 $g/m^2$. In addition, the film used in the present invention also has an MVTR of from about 5800 to about 10000 $g/m^2/24$ hrs, from about 5900 to about 6300 $g/m^2/24$ hrs, or about 6000 $g/m^2/24$ hrs.

Porous films include a first major length-wise dimension or direction, and a second major, generally cross-wise dimension or direction that is substantially perpendicular to the first dimension. Porous films also have a third dimension or direction that extends along the bulk thickness of the film and is substantially perpendicular to both the first and second major directions.

The backsheet may be fixed or otherwise adhered to the surface of the absorbent core overall or in discrete zones of attachment. The backsheet may be adhered to the cover in an overlapping configuration, for example, parallel to the sides of the absorbent structure, parallel to the bottom of the absorbent article or in a flange seal extending from the sides of the absorbent structure. When the cover and backsheet are adhered to each other in a flange seal, the cover may additionally be wrapped around the flange seal about the cover; or the backsheet may additionally be wrapped around the flange seal about the cover.

The absorbent article may optionally have a multi-layered structure that may additionally contain a transfer layer, which is a low density fluid accepting and fluid releasing layer, that is usually located between the cover and the absorbent core. The transfer layer may be made of relatively less hydrophilic materials and structures than is contained in the absorbent core, such as of webs of meltblown polypropylene or polyester fibers. Such webs may also contain woodpulp entrained within. Transfer layers may also be made of low density, highloft nonwoven web of woodpulp and synthetic fibers, such as polyethylene, polypropylene, polyester, polyacrylonitrile, and polyamide. Such highloft webs may be bonded with chemical binders or by thermal means such as by through-air bonding.

The layers of the article may be attached or adhered to one another to form a cohesive unit to enhance the article's stability. Such attachment or adherence may be by any known means, including, for example, adhesive, ultrasonics, co-embossing, thermobonding, mechanical bonding, and the like. However, the adhesive does not inhibit the vapor transmission or breathability of the backsheet. In the case of a pantyliner, a construction adhesive is present between the cover and the absorbent core and also present between the absorbent core and the backsheet. The construction adhesive serves to hold the layers together and to minimize deformation during use. The adhesive can be applied as either a thin porous film or in a random spray, in a controlled spiral pattern, or in any other application pattern. See, for example, U.S. Pat. Nos. 5,462,538; 5,681,305 and 5,885,681, the disclosures of which are herein incorporated by reference in their entirety.

The absorbent article, in the case of a sanitary napkin or pantyliner, may be applied to the crotch of underpants by placing the backsheet of the absorbent article against the inside of the crotch of the underpants. Pressure sensitive adhesive may be applied to the outer surface backsheet of the absorbent article to help maintain it in place. As used herein, the term "pressure-sensitive adhesive" refers to any releasable adhesive or releasable tenacious means. Suitable pressure sensitive adhesives include, for example, water-based adhesives such as acrylate adhesives. Alternatively, the adhesive may be a rapid setting thermoplastic "hot melt" rubber adhesive or two-sided adhesive tape.

A paper release strip that has been coated on one side, may be applied to protect the adhesive on the backsheet prior to use. The coating on the release paper, for example, silicone, reduces adherence of the coated side of the release to the backsheet adhesive. The release strip can be formed from any suitable sheet-like material that, when coated, adheres with sufficient tenacity to the adhesive to remain in place prior to use, but can be readily removed when the absorbent article prior to placement on the wearer's underpants.

The absorbent articles of the present invention can be of various shapes and configurations depending on the intended end use, e.g., as disposable diapers, sanitary napkins, pantiliners, tampons, underpads, surgical dressings or wipes, and the like. Additionally, the present absorbent articles can be incorporated into a disposable or limited use garment as an integral part thereof. For example, an absorbent article made according to the present invention can be a part of disposable training pants and similar garments.

The thickness of the absorbent core may be uniform throughout the expanse of the absorbent element or, for the purpose of specific fit, flexibility and absorbency requirements, the absorbent core may be thicker in some regions than in others. For example, a embodiment has thickness profile wherein an absorbent core is thicker in the central region than it is in the end regions. Additionally, while any thickness of absorbent core is contemplated to be used in the instant invention, an embodiment includes an absorbent core that is thin, i.e., having a caliper thickness of less than about 5 mm, less than about 3.5 mm, or less than about 2.3 mm.

Any or all of the cover, absorbent core, transfer layer, backsheet, and adhesive may be colored. Such coloring includes, but is not limited to, white, black, yellow, blue, orange, green, violet, combinations thereof, and the like. Color may be imparted according the present invention though printing, dying, pigmentation, and/or filler particles. Colorants used according the present invention include dyes and inorganic and organic pigments. The dyes include, but are not limited to, Azo dyes (e.g., Solvent Yellow 14, Disperse Yellow 23, Metanil Yellow), anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like.

Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

Absorbent articles within the scope of this invention also include wound care articles such as bandages, including adhesive bandages. Adhesive bandages usually have a backsheet of perforated plastic or of a woven or knit fabric. The backsheet is covered completely or partially on one side with a pressure sensitive adhesive. An absorbent core is placed in the center of and adhered to the adhesive side of the backing material. The absorbent core typically lies between a cover, which contacts the skin and prevents the absorbent from sticking to the wound, and the backsheet.

In the description above and in the following non-limiting examples, the following methods were employed to determine various reported characteristics and properties.

The basis weight was reported by the manufacturer as being 30 g/m$^2$.

MVTR was determined by the following method: an environmental chamber was provided and maintained at 37+/−1° C. and a relative humidity of ~10%. Film Samples were then preconditioned in the environmental chamber to maintain moisture levels. 10 ml of DI water as added to a Payne Cup, e.g., a metal cup with an exposed surface of 10 cm. A preconditioned film sample was place over the flange of the cup. The sample was then clamped or sealed to the Payne Cup. The Payne Cup with sample were weighed. After weighing, the Payne Cup with sample were placed in the environmental chamber, which was maintained at 37° C. and 10% RH. After 24 hours, the Payne Cup with sample were allowed to cool to room temperature. After cooling, the Payne Cup with sample were reweighed. MVTR was calculated using the following formula: Initial Weight−Final Weight*1000=MVTR.

The foregoing description is intended as illustrative and are not to be taken as limiting. Still other variations are possible without departing from the spirit and scope of this invention and will readily present themselves to one skilled in the art.

I claim:

1. An absorbent article comprising an absorbent core, a garment-facing breathable film backsheet, and a body-facing cover wherein said cover joins with said backsheet to encapsulate said absorbent core, and wherein the backsheet has a moisture vapor transmission rate ("MVTR") of from about 5800 to about 10000 g/m$^2$/24 hrs. and basis weight of less than about 32 g/m$^2$.

2. An absorbent article of claim 1, wherein, the MVTR of from about 5900 to about 6300 g/m$^2$/24 hrs.

3. An absorbent article of claim 2, wherein, the MVTR of about 6000 g/m$^2$/24 hrs.

4. An absorbent article of claim 1, wherein the basis weight is from about 28 to about 32 g/m$^2$.

5. An absorbent article of claim 1, wherein the basis weight is about 30 g/m$^2$.

6. An absorbent article of claim 1, further comprising a transfer layer.

7. An absorbent article of claim 1, further comprising a transfer layer wherein said transfer layer is situated in between said cover and said absorbent core.

8. An absorbent article of claim 1, further comprising a release paper.

9. An absorbent article of claim 1, wherein the absorbent article is selected from the group consisting of a disposable diaper, sanitary napkin, an incontinence device, a surgical dressing, and an adhesive bandage.

10. An absorbent article of claim 9, wherein the absorbent article further comprises a color selected from the group consisting of white, black, yellow, blue, orange, green, violet, and mixtures thereof.

11. An absorbent article comprising an absorbent core, a garment-facing breathable film backsheet, a body-facing cover wherein said cover joins with said backsheet to encapsulate said absorbent core, and wherein the backsheet has a moisture vapor transmission rate ("MVTR") of about 6000 and a basis weight of about 30 g/$^2$.

12. An absorbent article of claim 11, further comprising a transfer layer.

13. An absorbent article of claim 11, further comprising a transfer layer wherein said transfer layer is situated in between said cover and said absorbent core.

14. An absorbent article of claim 11, further comprising a release paper.

15. An absorbent article of claim 11, wherein the absorbent article is selected from the group consisting of a disposable diaper, sanitary napkin, an incontinence device, a surgical dressing, and an adhesive bandage.

16. An absorbent article of claim 15, wherein the absorbent article further comprises a color selected from the group consisting of white, black, yellow, blue, orange, green, violet, and mixtures thereof.

* * * * *